US012661643B2

(12) United States Patent (10) Patent No.: US 12,661,643 B2
Ramprasad (45) Date of Patent: Jun. 23, 2026

(54) MODIFIED ZEOLITE CATALYST COMPOSITIONS AND METHODS OF USE

(71) Applicant: W.R. Grace & Co.-Conn., Columbia, MD (US)

(72) Inventor: Dorai Ramprasad, Columbia, MD (US)

(73) Assignee: W.R. Grace & Co.-Conn., Columbia, MD (US)

( * ) Notice: Subject to any disclaimer, the term of this patent is extended or adjusted under 35 U.S.C. 154(b) by 1001 days.

(21) Appl. No.: 17/773,490

(22) PCT Filed: Oct. 20, 2020

(86) PCT No.: PCT/US2020/056412
§ 371 (c)(1),
(2) Date: Apr. 29, 2022

(87) PCT Pub. No.: WO2021/086679
PCT Pub. Date: May 6, 2021

(65) Prior Publication Data
US 2024/0165600 A1 May 23, 2024

Related U.S. Application Data

(60) Provisional application No. 62/956,828, filed on Jan. 3, 2020, provisional application No. 62/927,255, filed on Oct. 29, 2019.

(51) Int. Cl.
| | |
|---|---|
| *B01J 37/26* | (2006.01) |
| *B01J 21/04* | (2006.01) |
| *B01J 21/16* | (2006.01) |
| *B01J 29/40* | (2006.01) |
| *B01J 35/40* | (2024.01) |
| *B01J 37/02* | (2006.01) |
| *B01J 37/08* | (2006.01) |
| *C07D 211/02* | (2006.01) |

(52) U.S. Cl.
CPC .............. *B01J 37/26* (2013.01); *B01J 21/04* (2013.01); *B01J 21/16* (2013.01); *B01J 29/405* (2013.01); *B01J 35/40* (2024.01); *B01J 37/0205* (2013.01); *B01J 37/0236* (2013.01); *B01J 37/08* (2013.01); *C07D 211/02* (2013.01); *B01J 2229/16* (2013.01); *B01J 2229/186* (2013.01); *B01J 2229/42* (2013.01)

(58) Field of Classification Search
CPC ... B01J 37/26; B01J 35/40; B01J 21/04; B01J 21/16; B01J 29/405; B01J 37/0205; B01J 37/0236; B01J 37/08; B01J 2229/16; B01J 2229/186; B01J 2229/42; C07D 211/02
See application file for complete search history.

(56) References Cited

U.S. PATENT DOCUMENTS

| | | | | |
|---|---|---|---|---|
| 3,917,542 | A | 11/1975 | Beschke et al. | |
| 4,220,783 | A | 9/1980 | Chang et al. | |
| 4,711,770 | A * | 12/1987 | Skeels | C01B 39/026 502/79 |
| 4,996,034 | A * | 2/1991 | Skeels | C01B 39/026 423/709 |
| 5,080,878 | A * | 1/1992 | Bowes | C10G 50/02 585/407 |
| 5,218,122 | A * | 6/1993 | Goe | C07D 213/08 546/253 |
| 5,733,535 | A | 3/1998 | Hollingshead et al. | |
| 6,200,463 | B1 * | 3/2001 | Wilson | C10G 11/05 423/713 |
| 2005/0101819 | A1* | 5/2005 | Galperin | B01J 29/06 502/263 |
| 2015/0239841 | A1 | 8/2015 | Ramprasad | |

FOREIGN PATENT DOCUMENTS

| | | |
|---|---|---|
| JP | S50-145277 A | 11/1975 |
| JP | 2015-535254 A | 12/2015 |
| WO | WO-2011/072469 A1 | 6/2011 |

OTHER PUBLICATIONS

Xu; Journal of Catalysis 2012, 295, 232-241. (Year: 2012).*
Le Van Mao; Applied Catalysis A: General 1999, 185, 41-52. https://doi.org/10.1016/S0926-860X(99)00132-5 (Year: 1999).*
Louis; Microporous and Mesoporous Materials 2004, 74, 171-178. https://doi.org/10.1016/j.micromeso.2004.06.016 (Year: 2004).*
Luo; Reac Kinet Mech Cat 2018, 125, 365-380, with supplementary material. https://doi.org/10.1007/s11144-018-1405-1 (Year: 2018).*
Zhang; Catalysis Communications 2016, 80, 10-14. https://doi.org/10.1016/j.catcom.2016.02.011 (Year: 2016).*
Notification of Reasons for Rejection from JP Patent Application No. 2022-524918, dated Jun. 7, 2023.
International Search Report and Written Opinion from PCT/US2020/056412 dated Feb. 2, 2021, 9 Pages.
He, Peng et al., "Impact of Al sites on the methane co-aromatization with alkanes over Zn/HZSM-5," Catalysis Today, 323, 2019, pp. 94-104.
First Examination Report on IN patent appl. No. 202217029229 dated Sep. 8, 2022 (5 pages).

* cited by examiner

*Primary Examiner* — Daniel R Carcanague
(74) *Attorney, Agent, or Firm* — Dority & Manning, P.A.

(57) ABSTRACT

A modified zeolite catalyst composition is disclosed formed from a zeolite, alumina binder, and matrix. The modified zeolite catalyst composition may contain fluorine. Also disclosed, are methods for the preparation of pyridine and/or its alkylpyridine derivatives in high yield utilizing the modified zeolite catalyst composition.

14 Claims, No Drawings

MODIFIED ZEOLITE CATALYST COMPOSITIONS AND METHODS OF USE

RELATED APPLICATIONS

The present application is the U.S. National Stage of International Patent Application No. PCT/US2020/056412, filed on Oct. 20, 2020, which claims priority to U.S. Provisional Patent application Ser. No. 62/927,255, filed on Oct. 29, 2019, and U.S. Provisional Patent application Ser. No. 62/956,828, filed on Jan. 3, 2020, both of which are incorporated herein by reference.

BACKGROUND

Pyridine and pyridine derivatives can be synthesized from the reaction of aldehydes, ketones, and ammonia. For example, acetaldehyde, formaldehyde, and ammonia can be reacted over a heterogenous catalyst to give pyridine and beta-picoline whereas acetaldehyde and ammonia can be reacted to give alpha- and gamma-picoline. Other ketones, such as acetone, may be used to make 2,6-dimethyl pyridine and 2,4,6-trimethylpyridine. Certain catalysts, such as zeolite catalysts may be used during the production of pyridine and pyridine derivatives.

In the past, zeolite catalysts have been developed which afford higher catalytic activity when utilized in reactions designed to produce pyridine and pyridine derivatives. However, given the need for increased production of pyridine and its derivatives, such as certain isomers of picoline, there is a need for a modified zeolite catalyst composition capable of producing greater yields of pyridine and its derivatives.

SUMMARY

The present disclosure is generally directed to a modified zeolite catalyst composition that contains a zeolite, an alumina binder, and matrix containing kaolin. The modified zeolite catalyst composition has been modified to contain from about 0.5% to about 4.5% by weight of fluorine. The modified zeolite catalyst composition provides improved yields of pyridine and its derivatives when utilized. It was unexpectedly discovered that the modified zeolite catalysts provided herein improve total pyridine yield as compared to other zeolite catalysts that have not been modified according to the example embodiments disclosed herein.

Also provided herein are methods for the preparation of pyridine or its alkylpyridine derivative in high yield. The method includes reacting a $C_2$ to $C_5$ aldehyde, a $C_3$ to $C_5$ ketone or a mixture thereof, with ammonia and, optionally formaldehyde, and in the presence of an effective amount of a modified zeolite catalyst composition comprising a zeolite, an alumina binder, and kaolin, wherein at least one of the zeolite, alumina binder, or kaolin has been treated with one or more ions of or compounds containing fluorine, wherein the modified zeolite catalyst composition comprises from about 0.5% by weight to about 4.5% by weight of fluorine.

Other features and aspects of the present disclosure are discussed in greater detail below.

DETAILED DESCRIPTION

Before describing several exemplary embodiments, it is to be understood that the invention is not limited to the details of construction or process steps set forth in the following description. The invention is capable of other embodiments and of being practiced or being carried out in various ways.

In general, the present disclosure is directed to a modified zeolite catalyst composition for producing pyridine and pyridine derivatives in high yields. The present disclosure is also directed to methods of preparing pyridine or pyridine derivatives in high yield using the modified zeolite catalyst composition disclosed herein. In general, the modified zeolite catalyst composition of the present disclosure contains a zeolite that is combined with an alumina binder and kaolin. The modified zeolite catalyst composition has been treated such that it contains from about 0.5% to about 4.5% by weight of fluorine. Without being bound by any particular theory, the modified zeolite catalyst composition disclosed herein exhibits higher pyridine and pyridine derivative yields when utilized according to the methods disclosed herein as compared to other known methods.

Processes to produce bases of pyridine or alkylpyridine derivatives are prepared by reacting aldehydes and/or ketones with ammonia in the gas phase and/or liquid phase using a heterogeneous catalyst. Some examples of base synthesis reactions (and their common names where appropriate) include: the synthesis of pyridine and beta-picoline from acetaldehyde and formaldehyde (the "pyridine-beta reaction"); the synthesis of alpha- and gamma-picoline from acetaldehyde (the "alpha-gamma reaction"); the synthesis of 2,6-dimethylpyridine ("2,6-lutidine") from acetone and formaldehyde; the synthesis of 2,4,6-trimethylpyridine ("sym-collidine") from acetone alone or with acetaldehyde; the synthesis of pyridine and beta-picoline from acrolein alone or with acetaldehyde; the synthesis of 3,5-dimethylpyridine from propionaldehyde and formaldehyde; and the synthesis of beta-picoline from acetaldehyde, formaldehyde and propionaldehyde. Other methods are known, that include one or more of the reactants in the liquid phase. Many others are known and reported or practiced in the art and are equally considered within the scope of the description provided herein.

The catalysts used in these pyridine base synthesis reactions have varied from alumina which was used either alone or as a support for zinc fluoride or other metal salts to an amorphous structure incorporating both silica and alumina which became an important commercial catalyst. For example, alumina has been utilized either alone or as a support for certain catalysts. Similarly, the reactor designs for these heterogeneous gas-phase reactions have varied within the basic categories of fixed-bed and fluid-bed forms. One reason for the use of fluid bed reactors is that base synthesis reactions produce deposits of dark, mostly carbonaceous materials referred to as "coke" which tend to foul the catalyst thereby gradually reducing its activity. Although variations are observed, all catalysts accumulate these coke deposits at an appreciable rate such that periodic action is required. As discarding catalyst is not desirable for economic reasons, regeneration by heating in air or other oxygen-containing gases is commonly employed. This regeneration/combustion process is very exothermic and best carried out in a fluid bed process.

Accordingly, a common technique has long been to run two fluid beds concurrently, one for reaction and one for regeneration, with catalyst continuously or intermittently cycled between the beds. Operating parameters such as circulation rates, contact times, temperatures and the like are readily determined by skilled operators in view of the specific reactions and/or ingredients used. An ancillary benefit of this technique is that product yields from base synthesis reactions carried out in fluidized beds are recognized to be generally higher than in corresponding fixed-bed reactions. This was emphasized in two families of patents issued to BP Chemicals U.K. Ltd. of London, England, one for alpha-gamma synthesis (British Patent No. 1,188,891; German Patent 1,903,879; and Canadian Patent No. 852 745) and the other for pyridine-beta synthesis (British Patent No. 1,235,390; Canadian Patent No. 851,727; and German Patent No. 1,903,878). These BP patents, and German Patent No. 1,903,878 in particular, compare fixed- and fluid-bed reactions using catalysts of amorphous silica-alumina or of metal compounds such as the oxides or fluorides of lead, zinc and cadmium on amorphous silica-alumina supports.

Another technique includes utilizing a fluid bed in a cyclic mode. For instance, the feed containing certain reagents may be exposed to the catalyst composition particles in a fluid bed reactor as described in U.S. 2011/0108462, incorporated herein by reference. For example, catalyst composition particles may be lifted upwardly through a riser reaction zone, fluidized and mixed with the desired hydrocarbon feed/reagents. After reaction, coke laden catalyst composition particles or deactivated catalyst composition particles may be sent to a regenerator where they are reactivated by burning off carbonaceous deposits in the presence of oxygen. Regeneration may be carried out at temperatures between 450° C. and 650° C. in the presence of air and may be in the presence of an oxidizing catalyst additive. This process may allow for more thorough coke removal. Once stripped of coke deposits, the regenerated catalyst particles can then be sent back to the riser reactor for further use. This cycle may be repeated numerous times depending on catalyst activity, reactor throughput requirement, mechanical strength of catalyst particles, and cost of catalyst.

Certain base synthesis reactions have received universal acceptance as evidenced by their continuous commercial use for many years. The products of base synthesis, including pyridine, alpha-, beta- and gamma-picoline, nearly all the lutidines, and primarily the symmetrical isomer of collidine, have all shown commercial importance in the world chemical market albeit of varying values and volume requirements. It is also the case that improvement in the yields of these reactions and variation in their product ratios may be desirable according to market trends for such pyridine-derivative products as the herbicide paraquat, vitamins such as niacin and niacinamide, tire cord adhesive derived from 2-vinylpyridine, the tuberculosis drug Isoniazid, and so forth. One approach to this end has examined variations in reaction conditions such as temperature, velocity or contact time, mole ratios of feed stocks, and the like. Here, optimization of yield or product ratio is generally accomplished by known techniques employed by those skilled in this area.

For example, certain so-called shape-selective zeolites which are aluminosilicates of definite crystal structure having activities and pore sizes similar to that of other commercially-interesting molecules have been studied. These materials are often defined by a constraint index which is an experimentally-derived number based on the observed relative rates of reaction of straight and branched-chain molecules. Frillette et al., J. Catal., 67, 218 (1981). The term "zeolite" has even acquired a broader meaning in the art and is accordingly used in this application to mean more than the original crystalline aluminosilicate materials. For example, "zeolite" is understood and meant to also include compositions such as gallosilicates, ferrosilicates, chromosilicates and borosilicates. Crystalline aluminum phosphates ("ALPO's") and silicon-aluminum phosphates ("SALPO's") are also included in its coverage because of their catalytic ability, as is even theoretically-pure crystalline silicalite such as the S-115 material marketed by Union Carbide Corporation of N.Y.

Accordingly, the present disclosure provides for a modified zeolite catalyst composition that can be advantageously modified with a fluorine containing compound that will give improved and selective product yield. Furthermore, the yield of both pyridine and picoline can be improved via utilization of the modified zeolite catalysts described herein. For example, certain other processes may improve the yield of pyridine but to the detriment of the yield of picoline derivatives.

Example embodiments of the present disclosure are directed to a modified zeolite catalyst composition. The modified zeolite catalyst composition may include at least one zeolite. Suitable zeolites may include those that are commercially available. For example, in some embodiments the modified zeolite catalyst may include a zeolite that comprises a crystalline aluminosilicate or other substituted-silicate material having a constraint index of from about 1 to about 12. "Constraint index" is a conventional term of art which is defined, e.g., in Frillette et al, Journal of Catalysis, 67, 218-222 (1981), whose disclosure is entirely incorporated by reference herein. This parameter is fully sufficient to define those catalysts that will have a microstructure suitable for use in the process of this invention, i.e., it defines those catalysts having pore characteristics such that the necessary constrained access to the interior of the catalyst is provided.

Constraint index (C.I.) values for some typical zeolites are given in the table below.

| Aluminosilicate | Constraint Index |
|---|---|
| ZSM-5 | 8.3 |
| ZSM-11 | 8.7 |
| ZSM-12 | 2 |
| ZSM-38 | 2 |
| ZSM-35 | 4.5 |
| TMA Offretite | 3.7 |
| Clinoptilolite | 3.4 |
| S-115 | About 1 |
| Zeolite Beta | 0.6 |
| Zeolite Omega | 0.5 |
| H-Zeolon (mordenite) | 0.4 |
| REY | 0.4 |
| Amorphous Silica-Alumina | 0.6 |
| Erionite | 38 |

In certain embodiments, the selected zeolite may have a high atomic amount or ratio of silica to alumina or other substituted-metal ions in its structure. For example, in some embodiments the zeolite may have a silica to alumina ratio of from about 5 to 100. In some embodiments, the zeolite may have a silica to alumina ratio of from about 20 to about 60. In some embodiments, the zeolite may have a silica to alumina ratio of from about 30 to about 50. In some embodiments the zeolite may have a silica to alumina ratio of about 28. In some embodiments, the zeolite may have a silica to alumina ratio of about 55. The mentioned silica to alumina ratio can be fully conventionally determined using routine methods of analysis. See, e.g., Bibby et al, J. Catalysis, 72, 373-374 (1981), whose disclosure is entirely incorporated by reference herein. This ratio, as is fully conventional, refers, as closely as possible, to the ratio in the rigid crystalline framework of the zeolite crystal. The aluminum in the catalyst carrier or binder and in cationic or other form within the catalyst's channels, is excluded, as is well known. Methods for determining certain atomic amounts of silica, alumina, or other substitute metal ions in the structure can be fully conventionally determined using routine methods of analysis. See, e.g., "Zeolite Characterization and Catalysis—A Tutorial" (Editors: Arthur W. Chester, E. G. Derouane) ISBN: 978-1-4020-9677-8, whose disclosure is entirely incorporated by reference herein. Any known or conventional method may be utilized to determine the atomic amounts disclosed herein.

In some embodiments, the zeolite may contain a ZSM catalyst such as ZSM-5, ZSM-6, ZSM-7, ZSM-8, ZSM-9, ZSM-10, ZSM-11, ZSM-12, ZSM-35, ZSM-43, ZSM-48, and combinations thereof.

The zeolite catalysts suitable for use in this invention are also understood to include not only crystalline aluminosilicate zeolites possessing x-ray crystallinity but also those possessing x-ray amorphism and possessing infrared crystallinity as defined and disclosed in Jacobs et al, J.C.S. Chem Comm, 1981, 591-593, whose disclosure is entirely incorporated by reference herein. Similarly, the suitable zeolites are understood to include those in which various, usually trivalent, metals, e.g., boron, are apparently substituted for at least a portion of the aluminum in the crystal structure e.g., boron, arsenic, antimony, vanadium, iron or chromium. Such zeolites include those disclosed in DOS Nos. 28 30 787, 28 30 830, 28 31 611, 28 31 630, 28 31 631, and 29 09 929. Such zeolites can even no longer contain aluminum. (DOS No. 2830787—examples 1-6, 12 and 13: 100 mole % Al, examples 7-8: 100 mol % B, example 9: 100 mol % As, example 10, 100 mol % Sb; DOS No. 2831611—example 1: 75 mol % Fe, example 2: 85 mol % Fe, example 3: 90 mol % Fe; DOS No. 2831630—example 1: 58 mol % Cr, Example 2: 72 mol % Cr, Example 3: 83 mol % Cr; DOS No. 2831631—Example 1: 65 mol % V; DOS No. 2830830—38 mol % As; DOS No. 2909929—75 mol % B).

In certain embodiments, the zeolite may comprise a zeolite catalyst that has been modified with at least one metal, such as tungsten, zinc, tin, thallium, lead, cobalt, and combinations thereof. Once a zeolite is selected, a modified zeolite can be made by effectively modifying the zeolite material through treatment with one or more of the preferred metal ions of tungsten, zinc, tin, or compounds containing the same. This treatment may be carried out in any number of ways known in the art and may be carried out several times if desired to ensure substantial metal uptake on the zeolite. For example, suitable treatment processes are described in U.S. Pat. No. 5,218,122, incorporated herein by reference.

For example, one method of treatment is to add the zeolite to an aqueous solution of the desired tungsten, zinc or tin compound in stoichiometric excess and then to heat the mixture for some time at a predetermined temperature accompanied by stirring. The metal compounds used are soluble salts such as ammonium tungstate in the case of tungsten and nitrates, halides or acetates in the case of zinc or tin. This is followed by filtering, rinsing and drying, and then calcining at elevated temperature to obtain the finished catalyst. An alternate or possible further procedure is to prepare a physical mixture of the zeolite and the desired metal salt either dry or in the presence of enough water to constitute a paste or similar consistency, and then to complete the modification by blending or other suitable physical means. These and other similar procedures known in the, art are all within the scope, of the present disclosure.

As a result of this treatment procedure, an effective amount of the tungsten, zinc or in metal is taken up in the zeolite structure thereby modifying it to produce the improved catalyst in accordance with the present disclosure. The amount and method of this uptake will vary depending on many factors such as the identity and concentration of reactants, the specific treatment procedures and the like, all of which are within the skill of those experienced in this area to select and to control. For example, no minimum or threshold level of metal uptake is required with all amounts expected to produce some improved catalytic activity or effectiveness in later use. The same are therefore within the scope of the present disclosure so long as the characteristics described herein are met. Nevertheless, concentrations up to about 1.0 mg equivalent/g of the selected metal in the modified catalyst are obtainable and may be desired in a given circumstance.

In certain embodiments where the zeolite is selected from one that has been modified with at least one metal, the resultant modified zeolite catalyst composition may contain from about 1% by weight to about 3% by weight of the metal.

The modified zeolite catalyst composition disclosed herein may contain from about 20% by weight to about 50% by weight of zeolite. In certain embodiments, the modified zeolite catalyst composition may contain from about 30% to about 40% by weight of a zeolite, such as about 40% by weight of zeolite. For example, U.S. Pat. No. 4,675,410, incorporated herein by reference, discloses certain catalyst compositions that contain from about 5-80%, such as 20-50% by weight of the composition. In another example, U.S. Pat. No. 7,442,664, incorporated by reference herein, discloses a zeolite catalyst slurry composition that contains from about 10-70% by weight, more preferably about 50 wt %, and most preferably about 15-40 wt % of zeolite. Additionally, catalyst compositions containing greater than 50% of zeolite may produce a fine particulate zeolite that does not bind well with itself. Additionally, higher weight concentrations of zeolite in the finished catalyst composition can lead to a catalyst composition that is less attrition resistant. Methods for utilizing higher amounts of zeolite catalysts are known, such as those described by U.S. Pat. No. 4,675,410, which discloses use of up to 80% by weight of zeolite in the catalyst composition. In certain embodiments, compositions including greater than 50% by weight of zeolite may require additional binder in order to produce the modified zeolite catalyst compositions disclosed herein.

In some embodiments, the modified zeolite catalyst composition may contain a suitable binder. "Binder" is referred to the component or components added to the catalyst formulation that its presence has led to major improvement in catalyst ability to resist physical breakdown. Depending on the binder type, binder's function or effect may only be realized once it has gone through a physical and chemical transformation. For example, in certain embodiments an alumina binder, such as alumina sol is converted into a gamma alumina when it is calcined typically at temperatures higher than 500° C. Binders are important to provide mechanical strength to the finished catalyst composition particles. Suitable acceptable binders include colloidal alumina, colloidal silica, and their colloidal sols or precursors.

In certain embodiments, the binder may be an alumina binder. The alumina binder disclosed herein may include certain alumina binder compounds or alumina binder precursor compounds. Binders or binder precursors as provided herein, may include any material containing an alumina component that when processed according to the methods provided herein forms a binder to make a modified zeolite catalyst composition particle. Alumina binder precursor compounds may include those compounds that are precursors to binders and may require additional processing steps, such as calcination, to effectively bind together components of the modified zeolite catalyst compositions disclosed herein. For example, certain alumina binder precursors may be mixed with the zeolite, spray dried, and calcined in order to effectively bind the selected compounds of the modified zeolite catalyst compositions disclosed herein. In certain embodiments, the binder may include an alumina binder precursor. In certain embodiments, the alumina binder may include (pseudo)boehmite, gibbsite, heat-treated forms of gibbsite such as flash-calcined gibbsite, and combinations thereof. In certain embodiments, the alumina binder may include poly aluminum chloride. In certain embodiments, the alumina binder may include highly crystalline alumina. In certain embodiments, without being bound by any particular theory, the alumina binder may further provide mechanical strength to the modified zeolite catalyst by linking together zeolite crystallites.

In certain other embodiments, the modified zeolite catalyst composition may include a binder containing silica. Suitable silica compounds that may be included include, but are not limited to, silica, such as silica sol, sodium silicate, sodium-free silica, polysilicic acid, and combinations thereof.

In certain embodiments, the modified zeolite catalyst composition may contain from about 20% to about 50% by weight of a binder. In certain embodiments, the modified zeolite catalyst composition may contain from about 30% to about 40% by weight of a binder, such as about 40% by weight of a binder.

In certain embodiments, the modified zeolite catalyst composition may include a matrix. "Matrix" is referred to the material added to the catalyst composition that its introduction is not for activity enhancement nor binding enhancement, but rather, to increase particle density or to improve thermal stability through particle compaction. Known matrix materials used in catalyst composition formulations include kaolin clay and other clays or metal oxides. However, in some embodiments, matrix materials may also provide some level of catalytic activity. The matrix may be comprised of any suitable material. For example, in some embodiments, the matrix may include kaolin. In certain embodiments, the matrix may include any suitable clay including kaolin, bentonite, English clay, and heat- or chemically-treated clays such as meta-kaolin. In certain embodiments, the clay may have a low sodium content, such as below about 0.1 wt % $Na_2O$. In certain embodiments, the matrix may include anionic clays, such as hydrotalcite, saponite, montmorillonite, titanates (e.g. barium titanate, calcium titanate, magnesium titanate, and combinations thereof) calcium silicate, magnesium silicate, mixed metal oxides, layered hydroxy salts, and combinations thereof.

The modified zeolite catalyst composition may contain from about 20% to about 50% by weight of a suitable matrix. In certain embodiments, the modified zeolite catalyst composition contains from about 30% to about 40% by weight of a matrix, such as about 40% by weight of a matrix. In certain embodiments, the modified zeolite catalyst composition contains from about 35% to about 48% by weight of a matrix.

Optionally, the modified catalyst composition can also contain a zinc compound, such as zinc oxide. The zinc compound can be present in the modified zeolite catalyst in an amount generally less than about 5% by weight, such as in an amount less than about 3% by weight, such as in an amount less than about 2% by weight, and generally in an amount greater than about 0.1% by weight, such as in an amount greater than about 0.5% by weight, such as in an amount greater than about 1% by weight.

In certain embodiments, at least one of the zeolite, binder, matrix, or combinations thereof are treated with a suitable compound or composition containing fluorine. For example, in certain embodiments, the zeolite may be treated with a suitable fluorine containing compound or composition before being combined with the binder and the matrix. In certain embodiments, the binder may be treated with a suitable fluorine containing compound or composition prior to being combined with the zeolite and matrix. In still certain other embodiments, the matrix may treated with a suitable fluorine containing compound or composition prior to being combined with the zeolite and binder. Still in certain embodiments, the zeolite, binder, and matrix may be combined and then treated with a suitable fluorine containing compound or composition.

Suitable fluorine containing compounds or compositions include ammonium hexafluorosilicate, ammonium fluoride, zinc hexafluorosilicate, or combinations thereof. Any organic or inorganic fluoriding agent which can form a surface fluoride with alumina can be used according to the methods provided herein. Suitable fluoriding agents include, but are not limited to, hydrofluoric acid (HF), ammonium fluoride ($NH_4F$), ammonium bifluoride ($NH_4HF_2$), ammonium fluoroborate ($NH_4BF_4$), ammonium silicofluoride (($NH_4)_2SF_6$)), ammonium fluorophosphate ($NH_4PF_6$), and mixtures thereof. In certain embodiments, ammonium bifluoride may be preferred due to ease of use and availability. In certain embodiments, the fluorine containing compound may include organic fluoriding agents such as freons, perfluorohexane, perfluorobenzene, fluoromethane, trifluoroethanol, and mixtures thereof. Preferably, the fluorine containing compound is one that can be formulated and applied to the modified zeolite catalyst components or to components of the modified zeolite catalyst composition in liquid form.

In some embodiments, the modified zeolite catalyst composition that has been treated with a suitable fluorine containing compound may comprise from about 0.5% to about 4.5% by weight of fluorine. In still certain embodiments, the modified zeolite catalyst composition may contain from about 1.5% to about 2.5% by weight of fluorine. The percent (%) fluorine is calculated as (amount of F in the fluorine containing compound loaded on the catalyst/the weight of the catalyst)*100.

The modified zeolite catalyst composition may be prepared by combining a suitable zeolite with a binder and/or matrix and extruded or spray-dried to form spherical particles. For example, a zeolite may be combined with a binder, such as a suitable alumina binder or binder precursor, and matrix, and spray-dried to an appropriate particulate size and configuration for use in a fluidized-bed reactor. In certain embodiments, a zeolite may be spray-dried with an alumina binder and kaolin matrix to an appropriate particulate size and configuration for use in a fluidized-bed reactor. In certain embodiments, the zeolite, binder, and matrix may be combined to form a slurry. The slurry may then be milled or mixed for a certain period of time. After mixing or milling, the slurry containing the zeolite, binder, and matrix can then be spray-dried to an appropriate particulate size and configuration for use in a fluidized-bed reactor.

The modified zeolite catalyst composition may be contacted with one or more fluorine containing compounds. The one or more fluorine containing compounds may include ammonium fluorosilicate, ammonium fluoride, zinc hexafluorosilicate such as zinc hexafluorosilicate hydrate (e.g. $ZnSiF_6 \cdot 6H_2O$), and combinations thereof. In certain embodiments, the zeolite, binder, and matrix may be combined and then contacted with one or more suitable fluorine containing compounds. The modified zeolite catalyst composition may be contacted via an incipient wetness impregnation method with the fluorine containing compound. Incipient wetness impregnation may also be referred to as capillary impregnation or dry impregnation and is a known technique for the synthesis of catalyst compositions. In some embodiments, any of the zeolite, binder, or matrix may be contacted with one or more suitable fluorine containing compounds prior to being combined to form the modified zeolite catalyst composition. In certain embodiments, the modified zeolite catalyst composition may be exposed to multiple incipient wetness impregnation steps. For example, in certain embodiments, the modified zeolite catalyst composition may be prepared and contacted via an incipient wetness impregnation method with a fluorine containing compound, dried, and subsequently exposed to another incipient wetness impregnation method with a fluorine containing compound. The modified zeolite catalyst composition may be exposed to as many incipient wetness impregnations with a fluorine containing compound as required to achieve the desired fluorine concentration in the final modified zeolite catalyst composition. For example, if higher amounts of fluorine are desired in the modified zeolite catalyst composition, the modified zeolite catalyst composition may be subjected to multiple incipient wetness impregnations with a fluorine containing compound.

As indicated above, in one embodiment, the fluorine containing compound can be zinc hexafluorosilicate. The zinc hexafluorosilicate can be applied as a hydrate, such as zinc hexafluorosilicate hydrate. Using zinc hexafluorosilicate as the fluorine containing compound may provide various benefits and advantages. For example, the use of zinc hexafluorosilicate will incorporate zinc into the modified zeolite catalyst composition. Thus, the use of zinc hexafluorosilicate can incorporate zinc into the catalyst composition without having to additionally treat the catalyst composition with a zinc compound, such as a zinc oxide.

In certain embodiments, the modified zeolite composition may contain a zeolite combined with an alumina binder and matrix and spray-dried to form spherical particles. The zeolite, alumina binder, and kaolin may be combined to form a slurry and then may be milled and/or mixed. In certain embodiments, the spherical particles may contain one or more particles having an average diameter of from about 20 μm to about 100 μm. In certain embodiments, the spherical particles may contain one or more particles having an average diameter of from about 50 μm to about 90 μm. In certain embodiments, the spherical particles may contain one or more particles having an average diameter of from about 45 μm to about 90 μm. The size of the modified zeolite catalyst composition may be modified or configured to suit the desired type of reactor, i.e. a fixed bed or fluid bed reactor. Generally, for fluidization purposes the catalyst composition particles are in the form of microspheres. Too small particles (<20 microns) tend to be carried away from the reaction zone as fines of dust due to certain gas velocities employed. However, particles that are too large, i.e. those greater than 200 microns, can lead to hydrodynamic problems including poor mixing or poor catalyst distribution.

The modified zeolite catalyst composition may be prepared according to procedures described herein followed by drying and calcining. For example, after forming the modified zeolite catalyst composition, the composition may be dried in a vacuum oven at a temperature of from about 100° C. to about 140° C. for a drying time of from about 5 hours to about 12 hours. The modified zeolite catalyst composition may be calcined via any suitable method known in the art. For example, in certain embodiments, the modified zeolite catalyst composition is calcined at a temperature of about 550° C. for a time period of about 5 hours.

Advantageously, in certain embodiments, the modified zeolite catalyst composition may not be subjected to a calcining treatment procedure subsequent to drying. For example, the dried modified zeolite catalyst composition may be dried and immediately used in a suitable reactor, such as a fluid bed reactor. In some embodiments, the initial temperature of the reactor may be at or about 450° C. Accordingly, without being bound by any particular theory, exposing the dried catalyst composition directly to the reactor may facilitate calcining of the catalyst composition in the reactor itself. Accordingly, elimination of a separate calcining step reduces overall process time, thus the methods for producing the modified zeolite catalyst composition described herein may reduce processing times and are more economic than other methods. Additionally, elimination of the calcination step eliminates the need for an energy intensive step and, thus, the processes provided herein may be more economical as compared to other methods that require calcination. Furthermore, elimination of the calcination step may reduce certain fluorine contaminates that could be generated during calcination of the modified zeolite catalyst composition containing fluorine. During calcination, certain undesirable fluorine compounds could be generated and released from the modified zeolite catalyst composition. Such, fluorine compounds could lead to undesirable environmental hazards. For example, elimination of the calcination step could eliminate the formation of toxic hydrogen fluoride (HF) gas. Accordingly, elimination of additional calcinations steps, allows for use of the modified zeolite catalyst compositions disclosed herein without increasing potential environmental concerns.

Also provided herein are methods for the preparation of pyridine and/or its alkylpyridine derivatives in high yield. The method includes reacting a $C_2$ to $C_5$ aldehyde, a $C_3$ to $C_5$ ketone or a mixture thereof, with ammonia and, optionally formaldehyde, and in the presence of an effective amount of a modified zeolite catalyst composition comprising a zeolite, a binder, and matrix, wherein the modified zeolite catalyst composition comprises from about 0.5% by weight to about 4.5% by weight of fluorine. The reactants employable in the condensation reaction of this invention include $C_{2-5}$-aliphatic aldehydes which can be saturated or unsaturated and/or $C_{3-5}$-aliphatic ketones which can also be saturated or unsaturated in admixture with ammonia. Formaldehyde is an often preferred coreactant. A single aldehyde, a single ketone, mixtures of aldehydes, mixtures of ketones and mixtures of aldehydes and ketones may be employed.

In some embodiments, the feed is the combination of acetaldehyde, formaldehyde and ammonia. In other embodiments, the feed is the combination of crotonaldehyde, formaldehyde and ammonia.

The carbonyl compounds may be used as monomers, dimers, trimers, other oligomers or polymers, e.g., solid polymers, etc. Water can also be included in the reactant stream. For example, formaldehyde can be added to the reaction medium in the form of formalin, the water content of which is non-critical. Any conveniently available formalin, e.g., 10% formaldehyde, 50% formaldehyde, 90% formaldehyde, etc., can be employed. Also usable are the paraformaldehydes, s-trioxane, paracetaldehyde etc. Reactants are of ordinary commercial purity.

Depending upon the precise combination of reactants employed and the stoichiometry, various main product pyridine-type bases and combinations of such main products with side products can be achieved, as is well known. For example, the following table lists some of the many possibilities.

| Feed + NH3 | Principal Product |
| --- | --- |
| 2 acetaldehyde + 1 formaldehyde | Pyridine + β-picoline |
| 1 crotonaldehyde + 1 formaldehyde | Pyridine + β-picoline |
| 2 acrolein | β-picoline + 3,5-lutidine |
| 1 acrolein + 1 acetaldehyde | Pyridine + β-picoline |
| 1 acrolein + 1 acetone | Pyridine + α-picoline + β-picoline |
| 1 acrolein + 1 propionaldehyde | β-picoline + 3,5-lutidine |
| 2-propionaldehyde + 1 formaldehyde | 3,5-lutidine |
| 1 butyraldehyde + 1 acetaldehyde + 1 formaldehyde | 3-ethyl pyridine |
| 2 butyraldehyde + 1 formaldehyde + 3 acetaldehyde | 3,5-diethyl pyridine + α-, +β-, +γ-picoline |

Molar ratios of the reactants for any given combination are routinely determinable in accordance with the underlying stoichiometry of the reaction. For example, the molar ratio of acetaldehyde: formaldehyde: ammonia is usually within the following approximate limits, based upon the monomeric aldehydes per se—1:0.6-3:0.5-5; preferably 1:0.75-1.25:1-3. Typically, these molar ratios are 1:0.75-1:1-1.56. When water is included, generally, the molar ratio of water to acetaldehyde is up to 10, i.e., generally 0-10, usually 0-3. The amount thereof is essentially non-critical unless unreasonable dilutions are involved. For other feed combinations, analogous preferred molar ratios will be employed taking into account the ordinary conventional considerations.

The manner of mixing the gaseous reactants is also non-critical. Typically, for the preferred feed, the acetaldehyde and formaldehyde are added as a preformed mixture to the reactor. The ammonia is usually separately added. The manner of all additions is fully conventional.

Normally, it is preferred to carry out the reaction in the absence of $O_2$, e.g., air. Otherwise, difficult controls may be necessary to avoid explosive mixtures. Of course, if necessary or desirable, the reaction can be conducted in the presence of a small amount of air. Similarly, it is preferred that the reaction be conducted in the presence of only the mentioned reactants. Of course, other inert, system compatible materials may also be present. One such compound, often used in the past is methanol. In many prior art cases, the alkanol has been used as a reactant, e.g., as a substitute for formaldehyde. However, in the reaction of this invention and in some of the prior art reactions in which it was thought to be an active participant, methanol (and other alkanols for that matter) is inert with respect to pyridine and picoline products.

The process may be carried out in a fluidized or otherwise mobilized bed of the catalyst. Furthermore, the process may be carried out according to any desired reaction time. For example, the process may be carried out at a reaction time of at least 2 hours, such as at least 3 hours, such as at least 4 hours, such as at least 5 hours, such as at least 6 hours. In certain embodiments where the process is carried out in a fluid bed, the reaction may be continued as long as desired and catalyst may be regenerated according to any suitable method. The regenerated catalyst can then be sent back to the reactor for further and continuous use. In certain embodiments, additional catalyst may be fed to the reactor as necessary to continue the reaction and to continue reaction time.

The method provided herein may also produce unexpectedly favorable ratios of desired main products to undesired side products. For example, in the acetaldehyde/formaldehyde case, the primary product is pyridine and the primary side product is usually 3-picoline. Consequently, herein, the "ratios" refer to this most relevant ratio, i.e., the weight ratio of pyridine to 3-picoline. This invention provides ratio values in the range of about 1.5 to about 1.8, for the acetaldehyde/formaldehyde feed. Analogously high ratios will be attained for other feed combinations where applicable. These heretofore unachievable combinations of high total product yields and high ratios of desired main products to undesired side products represent a significant improvement over other methods.

As described above, the modified zeolite catalyst composition of the present disclosure can be used to produce pyridine and/or pyridine derivatives (i.e. picolines) in higher yields than previous methods. Furthermore, the modified zeolite catalyst compositions of the present disclosure have high catalyst activity and are well suited for use into reactor systems.

The present disclosure may be better understood with reference to the following examples.

EXAMPLES

Catalyst Preparation

ZSM-5 catalysts were treated with ammonium hexafluorosilicate or fluoride via the incipient wetness method using single or multiple impregnations. The catalyst compositions were dried in a vacuum oven at 120° C. overnight followed by calcination at 550° C. for about 5 hours. The % F was calculated as (amount of F in the fluorosilicate loaded on the catalyst/the weight of the catalyst)*100. Four different catalyst compositions Catalyst 1, Catalyst 2, Catalyst 3, and Catalyst 4, were prepared.

Catalyst 1=about 40% by weight of ZSM-5 (silica/alumina ratio of 28:1); about 12% by weight of alumina; and about 48% by weight of kaolin Catalyst 2=about 40% by weight of ZSM-5 (silica/alumina ratio of 28:1); about 12% by weight of alumina; about 48% by weight kaolin; and about 1.4% zinc oxide Catalyst 3=about 40% by weight of ZSM-5 (silica/alumina ratio of 55:1); about 12% by weight alumina; about 48% by weight of kaolin; and about 1.5% by weight of zinc oxide Catalyst 4=about 40% by weight of ZSM-5 (silica/alumina ratio of 28:1); about 12% weight alumina; about 48% by weight of kaolin Catalyst 1 containing 1.5% F was prepared according to the following steps: (1) prepare a saturated solution of ammonium hexafluorosilicate in water –0.1486 g/mL (2)

treat 125 g of catalyst (ZSM-5) with 20 mL of saturated ammonium hexafluorosilicate solution from (1) (3) dry catalyst in a vacuum oven at 120° C. overnight (4) calcine at 500° C. for 300 minutes and hold using a ramp of 1° C. per minute.

Catalyst 3 containing 2.5% F was prepared according to the following procedure. (1) weigh 150 g of finished ZnZSM-5 catalyst (2) impregnate 150 g of catalyst with 20 mL of saturated ammonium hexafluorosilicate solution (3) dry composition in an oven overnight at 120° C. (4) repeat step 2 (5) calcine catalyst composition at 550° C. for 30 minutes using a ramp of 1° C. per minute.

Catalyst 3 containing 2.5% F uncalcined—omits calcination step

Catalyst 4 (target 2.3% F) is prepared by pretreating zeolite with fluoride. 8.94 kg of ZSM 5(H+form) dry basis with silica/alumina ratio of 28 was weighed and to this was added 5.5 liters of solution containing 0.81 kg of ammonium hexafluorosilicate. The mixture was blended for an hour. To this was added 16 kg of water followed by 10.25 kg of aluminium chlorohydrol (26.3% alumina) followed by 10.77 kg of kaolin clay on dry basis. Mixture was milled and spray dried then calcined at 550 C for 300 minutes Catalyst Testing Procedure 100.0 g of catalyst were loaded into the fluid bed reactor. A 1.45 ml/min organics feed rate (240.9 g 99.5% acetaldehyde, 441.3 g 37% formaldehyde with 10-15% methanol solution in water) was accompanied by 395 SCCM NH$_3$ to perform the reaction. The organics pre-heater was set to 125° C., the furnace was set to 450° C., and the chiller/condenser was set to 1.0° C. The reaction proceeded for 6 hours with the first sample collected during the first hour, the second sample collected during the second hour, the third sample collected during the third and fourth hours, and the fourth sample collected during the fifth and sixth hours. At the end of six hours, the organics feed was stopped and replaced with DI water, which was fed to the reactor for 45 minutes to flush through any remaining organics in the feed line to the frit while NH$_3$ continued to flow. All product collected were analyzed by GC and yield were calculated on the basis of carbon atoms injected as formaldehyde and acetaldehyde and carbon recovered as pyridine and picolines. Yields calculated between 1-2 hours in reactor were used to draw conclusions

| Catalyst 1 | | | | | |
|---|---|---|---|---|---|
| Catalyst | Total yield % between 1-2 hours | Pyridine % | 2-picoline % | 3-picoline % | 4-picoline % | Pyridine/3-picoline selectivity |
| Catalyst 1 | 28.14 | 16.49 | 1.09 | 9.68 | 0.88 | 1.70 |
| Catalyst 1 (1.5% F) | 55.83 | 34.28 | 0.52 | 20.43 | 0.60 | 1.68 |

As shown, Catalyst 1 containing 1.5% F has an improved total pyridines yield of 55.83% versus 28.14% for the non-fluorided catalyst.

| Catalyst 2 | | | | | |
|---|---|---|---|---|---|
| Catalyst | Total yield % between 1-2 hours | Pyridine % | 2-picoline % | 3-picoline % | 4-picoline % | Pyridine/3-picoline selectivity |
| Catalyst 2 | 56.66 | 35.61 | 0.59 | 19.84 | 0.62 | 1.79 |
| Catalyst 2 (1.5% F) | 61.95 | 35.80 | 0.44 | 22.55 | 0.46 | 1.71 |

As shown, Catalyst 2 (1.5% F) has an improved total pyridines yield of 61.95% versus 56.66% for the non-fluorided catalyst.

| Catalyst 3 | | | | | |
|---|---|---|---|---|---|
| Catalyst | Total yield % between 1-2 hours | Pyridine % | 2-picoline % | 3-picoline % | 4-picoline % | Pyridine/3-picoline selectivity |
| Catalyst 3 | 56.20 | 33.94 | 0.39 | 21.44 | 0.43 | 1.58 |
| Catalyst 3 (1.5% F) | 63.37 | 38.70 | 0.36 | 23.90 | 0.41 | 1.62 |
| Catalyst 3 (2.5% F) | 64.28 | 39.97 | 0.34 | 23.60 | 0.37 | 1.69 |
| Catalyst 3 (2.5% F) uncalcined | 64.06 | 39.20 | 0.35 | 24.08 | 0.43 | 1.63 |
| Catalyst 3 (2.5% F)* | 64.02 | 39.35 | 0.30 | 24.04 | 0.33 | 1.64 |

*made with ammonium fluoride

As shown, fluorided Catalyst 3 shows yield improvements in the 7-8% range. Additionally catalyst can be activated in the reactor directly without calcination

| Catalyst 4 | | | | | |
|---|---|---|---|---|---|
| Catalyst | Total yield % between 1-2 hours | Pyridine % | 2-picoline % | 3-picoline % | 4-picoline % | Pyridine/3-picoline selectivity |
| Catalyst 4 (2.3% F) | 59.11 | 35.55 | 0.44 | 22.55 | 0.56 | 1.58 |

As shown catalysts with pretreatment of zeolite with F show very high activity.

Accordingly, the fluorided zeolite catalyst compositions show improved total pyridine yields in comparison with the control (i.e., non-fluorided catalyst composition).

The numbered statements hereinbelow provide example embodiments of the methods and compositions according to the present disclosure.

1. A method for the preparation of pyridine and/or its alkylpyridine derivatives in high yield comprising:

reacting a C$_2$ to C$_5$ aldehyde, a C$_3$ to C$_5$ ketone or a mixture thereof, with ammonia and, optionally formaldehyde, and in the presence of an effective amount of a modified zeolite catalyst composition comprising a zeolite, an alumina binder, and matrix, wherein at least one of the zeolite, alumina binder, or matrix has been treated with one or more ions of or compounds containing fluorine, wherein the modified zeolite catalyst composition comprises from about 0.5% by weight to about 4.5% by weight of fluorine.

2. The method of 1, wherein the zeolite has a constraint index of about 1 to 12.

3. The method of 2, wherein the zeolite comprises ZSM-5.

4. The method of 1, wherein the zeolite comprises a modified zeolite that has been modified by treatment with one or more metal ions or compounds of tungsten, zinc, or tin.

5. The method of 1, wherein the matrix comprises kaolin.

6. The method of 1, wherein the alumina binder has been treated with one or more compounds containing fluorine prior to being combined with the zeolite and matrix.

7. The method of 1, wherein the zeolite has been treated with one or more compounds containing fluorine prior to being combined with the alumina binder and matrix.

8. The method of 1, wherein the matrix has been treated with one or more compounds containing fluorine prior to being combined with the zeolite and alumina binder.

9. The method of 1, wherein the modified zeolite catalyst composition comprising a zeolite, an alumina binder, and matrix has been treated with one or more compounds containing fluorine.

10. The method of 1, wherein the modified zeolite catalyst composition comprises from about 1.5% by weight to about 2.5% by weight of fluorine.

11. The method of 1, wherein the modified zeolite catalyst comprises from about 30% to about 40% by weight of zeolite, from about 7% to about 12% by weight of alumina binder, and from about 35% to about 48% by weight of matrix.

12. The method of 1, wherein the one or more compounds containing fluorine are selected from the group consisting of ammonium fluorosilicate, ammonium fluoride, zinc hexafluorosilicate, and combinations thereof.

13. The method of 1, comprising loading the modified zeolite catalyst composition into a fluid bed reactor and exposing the $C_2$ to $C_5$ aldehyde, the $C_3$ to $C_5$ ketone or a mixture thereof, ammonia and, optionally, formaldehyde to the modified zeolite catalyst composition in the fluid bed reactor.

14. The method of 13, wherein the $C_2$ to $C_5$ aldehyde, a $C_3$ to $C_5$ ketone or a mixture thereof, ammonia and, optionally, formaldehyde are exposed to the modified zeolite catalyst in the fluid bed reactor for reaction time of at least 4 hours.

15. The method of 1, wherein the zeolite comprises a silica to alumina ratio of from about 20:1 to about 60:1.

16. The method of 1, wherein the modified zeolite catalyst composition comprises one or more particles, wherein the one or more particles have an average particle size of from about 20 μm to about 100 μm.

17. A modified zeolite catalyst composition, comprising:
   one or more particles comprising:
      a zeolite;
      an alumina binder;
      a matrix; and
      from about 0.5% by weight to about 4.5% by weight of fluorine, wherein the one or more particles have an average particle size of from about 20 μm to about 100 μm.

18. The composition of 17, wherein the zeolite comprises ZSM-5.

19. The composition of 17, wherein the alumina binder is selected from the group consisting of (pseudo)boehmite, gibbsite, heat-treated forms of gibbsite such as flash-calcined gibbsite, poly aluminum chloride, highly crystalline alumina, and combinations thereof.

20. The composition of 17, wherein the modified zeolite catalyst comprises from about 30% to about 40% by weight of zeolite, from about 7% to about 12% by weight of alumina, and from about 35% to about 48% by weight of matrix.

21. The composition of 17, wherein the matrix comprises kaolin.

22. The composition of 17, wherein the zeolite comprises a zeolite having a silica to alumina ratio of from about 20:1 to about 60:1.

23. The composition of 17, wherein the modified zeolite catalyst composition comprises from about 1.5% by weight to about 2.5% by weight of fluorine.

24. A method for preparing a modified zeolite catalyst composition, said method comprising the steps of:
   combining a zeolite with an alumina binder and matrix to form a catalyst composition;
   contacting the catalyst composition with one or more fluorine containing compounds to form a modified zeolite catalyst composition, wherein the modified zeolite catalyst composition comprises from about 0.5% by weight to about 4.5% by weight of fluorine; and
   drying the modified zeolite catalyst composition.

25. The method of 24, wherein the zeolite comprises ZSM-5.

26. The method of 24, wherein the alumina binder is selected from the group consisting of (pseudo)boehmite, gibbsite, heat-treated forms of gibbsite such as flash-calcined gibbsite, poly aluminum chloride, highly crystalline alumina, and combinations thereof.

27. The method of 24, wherein the fluorine containing compound is selected from ammonium fluorosilicate, ammonium fluoride, zinc hexafluorosilicate and combinations thereof.

28. The method of 24, wherein contacting the catalyst composition with the fluorine containing compound comprises contacting the catalyst composition via an incipient wetness method with the fluorine containing compound.

29. The method of 24, wherein drying the modified zeolite catalyst composition comprises drying the modified zeolite catalyst composition in a vacuum oven at a temperature of from about 100° C. to about 140° C. for a drying time of from about 5 hours to about 12 hours.

30. The method of 24, further comprising contacting the modified zeolite catalyst composition a second time with a fluorine containing compound after drying.

31. The method of 24, further comprising calcining the modified zeolite catalyst composition.

32. The method of 31, wherein the calcining the modified zeolite catalyst composition comprises calcining the modified zeolite catalyst composition at a temperature of about 550° C. for about 5 hours.

33. The method of 24, wherein combining the zeolite with an alumina binder and matrix comprises spray drying the zeolite with alumina binder and kaolin.

34. The method of 24, wherein combining the zeolite with an alumina binder and matrix comprises preparing a slurry comprising the zeolite, alumina binder, and matrix, and spray-drying the slurry to form one or more particles of the modified zeolite catalyst composition.

35. The method of 24, wherein the modified zeolite catalyst composition comprises from about 40% by weight of zeolite, from about 12% by weight of alumina, and from about 48% by weight of matrix.

36. A modified zeolite catalyst composition according to 24.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed is:

1. A method for the preparation of pyridine and/or its alkylpyridine derivatives in high yield the method comprising:

reacting a C2 to Cs aldehyde, a C3 to Cs ketone or a mixture thereof, with ammonia and, optionally formaldehyde, and in the presence of an effective amount of a modified zeolite catalyst composition comprising a zeolite, an alumina binder, and matrix, wherein at least one of the zeolite, alumina binder, or matrix has been treated with one or more ions of or compounds containing fluorine, wherein the one or more compounds containing fluorine comprise a fluorosilicate.

2. The method of claim 1, wherein the zeolite has a constraint index of about 1 to 12.

3. The method of claim 2, wherein the zeolite comprises ZSM-5.

4. The method of claim 1, wherein the zeolite comprises a modified zeolite that has been modified by treatment with one or more metal ions or compounds of tungsten, zinc, or tin.

5. The method of claim 1, wherein the matrix comprises kaolin.

6. The method of claim 1, wherein the alumina binder has been treated with one or more compounds containing fluorine prior to being combined with the zeolite and matrix.

7. The method of claim 1, wherein the zeolite has been treated with one or more compounds containing fluorine prior to being combined with the alumina binder and matrix.

8. The method of claim 1, wherein the matrix has been treated with one or more compounds containing fluorine prior to being combined with the zeolite and alumina binder.

9. The method of claim 1, wherein the modified zeolite catalyst comprises from about 30% to about 40% by weight of zeolite, from about 7% to about 12% by weight of alumina binder, and from about 35% to about 48% by weight of matrix.

10. The method of claim 1, wherein the fluorosilicate comprises ammonium fluorosilicate, zinc hexafluorosilicate, or combinations thereof.

11. The method of claim 1, comprising loading the modified zeolite catalyst composition into a fluid bed reactor and exposing the C2 to C5 aldehyde, the C3 to C5 ketone or a mixture thereof, ammonia and, optionally, formaldehyde to the modified zeolite catalyst composition in the fluid bed reactor.

12. The method of claim 11, wherein the C2 to C5 aldehyde, a C3 to C5 ketone or a mixture thereof, ammonia and, optionally, formaldehyde are exposed to the modified zeolite catalyst in the fluid bed reactor for reaction time of at least 4 hours.

13. The method of claim 1, where the zeolite comprises a silica to alumina ratio of from about 20:1 to about 60:1.

14. The method of claim 1, wherein the modified zeolite catalyst composition comprises one or more particles, wherein the one or more particles have an average particle size of from about 20 μm to about 100 μm.

* * * * *